US008628921B2

(12) United States Patent
Medo et al.

(10) Patent No.: US 8,628,921 B2
(45) Date of Patent: *Jan. 14, 2014

(54) METHODS FOR TESTING MILK

(75) Inventors: Elena M. Medo, Murrieta, CA (US);
Martin L. Lee, Studio City, CA (US);
David J. Rechtman, Hermosa Beach, CA (US)

(73) Assignee: Prolacta Bioscience Inc., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/592,678

(22) Filed: Aug. 23, 2012

(65) Prior Publication Data
US 2013/0064940 A1  Mar. 14, 2013

Related U.S. Application Data

(63) Continuation of application No. 13/079,932, filed on Apr. 5, 2011, now Pat. No. 8,278,046, which is a continuation of application No. 12/052,253, filed on Mar. 20, 2008, now Pat. No. 7,943,315, which is a continuation-in-part of application No. PCT/US2006/036827, filed on Sep. 20, 2006.

(60) Provisional application No. 60/719,317, filed on Sep. 20, 2005, provisional application No. 60/731,428, filed on Oct. 28, 2005.

(51) Int. Cl.
| C12Q 1/68 | (2006.01) |
| A23J 3/34 | (2006.01) |
| A23G 9/00 | (2006.01) |
| A23L 3/015 | (2006.01) |
| A23P 1/00 | (2006.01) |
| A01N 61/00 | (2006.01) |
| A01K 31/00 | (2006.01) |

(52) U.S. Cl.
USPC ............... 435/6.1; 426/7; 426/585; 426/665; 426/801; 514/1; 536/22.1

(58) Field of Classification Search
USPC ............. 435/6.1; 536/22.1, 23.1, 24.3; 426/7, 426/585, 665, 801; 514/1
See application file for complete search history.

(56) References Cited

U.S. PATENT DOCUMENTS

| 2,567,898 | A | | 9/1951 | Staaff |
| 3,946,113 | A | | 3/1976 | Seiberling |
| 4,282,265 | A | * | 8/1981 | Theuer ........................... 426/607 |
| 4,362,697 | A | | 12/1982 | Tabb et al. |
| 4,455,483 | A | | 6/1984 | Schonhuber |
| 4,753,926 | A | * | 6/1988 | Lucas et al. .................... 514/5.5 |
| 4,762,822 | A | | 8/1988 | Ettinger |
| 4,772,262 | A | | 9/1988 | Grant et al. |
| 4,876,100 | A | | 10/1989 | Holm et al. |
| 4,948,599 | A | | 8/1990 | Sagara et al. |
| 5,013,569 | A | * | 5/1991 | Rubin ........................... 426/585 |
| 5,064,674 | A | | 11/1991 | Girsh |
| 5,169,766 | A | | 12/1992 | Schuster et al. |
| 5,186,963 | A | * | 2/1993 | Howman ........................ 426/72 |
| 5,256,437 | A | | 10/1993 | Degen et al. |
| 5,303,598 | A | | 4/1994 | Binder et al. |
| 5,334,822 | A | | 8/1994 | Sanford |
| 5,401,523 | A | | 3/1995 | Degen et al. |
| 5,436,020 | A | * | 7/1995 | Kuwata et al. ................. 426/583 |
| 5,505,955 | A | | 4/1996 | Peterson et al. |
| 5,541,065 | A | | 7/1996 | Erlich et al. |
| 5,576,040 | A | | 11/1996 | Moller et al. |
| 5,605,689 | A | | 2/1997 | Ammann |
| 5,616,483 | A | | 4/1997 | Bjursell et al. |
| 5,670,196 | A | | 9/1997 | Gregory |
| 5,683,733 | A | | 11/1997 | Krabsen et al. |
| 5,686,491 | A | * | 11/1997 | Sherwood ...................... 514/561 |
| 5,707,678 | A | | 1/1998 | Gregory |
| 5,739,407 | A | * | 4/1998 | Bergstrom et al. ............... 800/7 |
| 5,795,611 | A | * | 8/1998 | Slattery ......................... 426/580 |
| 5,902,617 | A | * | 5/1999 | Pabst ............................. 426/61 |
| 5,972,337 | A | | 10/1999 | Ceriani et al. |
| 5,983,198 | A | | 11/1999 | Mowery et al. |
| 6,004,288 | A | | 12/1999 | Hochstedler et al. |
| 6,017,511 | A | | 1/2000 | Wong et al. |
| 6,020,015 | A | | 2/2000 | Gaull |
| 6,022,853 | A | * | 2/2000 | Kuberasampath et al. ... 424/464 |
| 6,056,978 | A | | 5/2000 | Beck et al. |
| 6,099,871 | A | * | 8/2000 | Martinez ........................ 426/2 |
| 6,183,803 | B1 | | 2/2001 | Morcol et al. |
| 6,194,009 | B1 | | 2/2001 | Kamarel |
| 6,222,094 | B1 | * | 4/2001 | Hansson et al. ................ 800/14 |

(Continued)

FOREIGN PATENT DOCUMENTS

| EP | 1637043 A1 | 3/2006 |
| GB | 1451747 A | 10/1976 |

(Continued)

OTHER PUBLICATIONS

"International Search Report," 2 pages, PCT appl. No. PCT/US2012/049590 (mailed Oct. 1, 2012).
"Written Opinion of the International Searching Authority," 6 pages, PCT appl. No. PCT/US2012/049590 (mailed Oct. 1, 2012).
Arnold, "How North American Donor Banks Operate: Results of a Survey: Part 1," J. Hum. Lact. 13(2):159-162 (1997).
Arnold, "How North American Donor Banks Operate: Results of a Survey: Part 2," J. Hum. Lact. 13(3):243-246 (Sep. 1997).
Arnold, "How to Order Banked Donor Milk in the United States: What the Health Care Provider Needs to Know," J. Hum. Lact. 14(1):65-67 (1998).
Bernshaw, "Milk Banking: An Idea That Has Come of Age. Non-Profit Milk Banking," Seminar delivered on Aug. 29, 2006. Retrieved from the internet: http://www.utahbreastfeeding.org/business/2006_08_MilkBankNotes.pdf.
Boehm, G., et al., "Metabolic Differences Between AGA- and SGA-Infants of Very Low Birthweight II Relationship to Protein Intake," Acta Pædiatrica Scandinavica, Almqvist, Och Wiksell, Stockholm, SE, vol. 77, No. 5, Jan. 1, 1988, pp. 642-646.

(Continued)

Primary Examiner — Ethan C Whisenant
(74) Attorney, Agent, or Firm — Cooley LLP

(57) ABSTRACT

The disclosure is related generally to methods for testing mammary fluid (including milk) to establish or confirm the identity of the donor of the mammary fluid. Such methods are useful in the milk-bank business to improve safety.

20 Claims, No Drawings

(56) References Cited

U.S. PATENT DOCUMENTS

| | | | |
|---|---|---|---|
| 6,270,827 B1 | 8/2001 | Gaull et al. | |
| 6,294,206 B1* | 9/2001 | Barrett-Reis et al. | 426/72 |
| 6,472,003 B2* | 10/2002 | Barrett-Reis et al. | 426/72 |
| 6,509,178 B1* | 1/2003 | Tanaka et al. | 435/134 |
| 6,613,367 B1 | 9/2003 | Wells et al. | |
| 6,635,296 B1 | 10/2003 | Nissen et al. | |
| 6,652,900 B2 | 11/2003 | Lindquist | |
| 6,670,124 B1 | 12/2003 | Chow et al. | |
| 6,737,096 B2 | 5/2004 | Lindquist | |
| 6,780,987 B1 | 8/2004 | Herman et al. | |
| 6,846,298 B1 | 1/2005 | Carr et al. | |
| 6,910,594 B2 | 6/2005 | Foley et al. | |
| 7,867,541 B2 | 1/2011 | McMahon et al. | |
| 7,914,822 B2 | 3/2011 | Medo | |
| 7,943,315 B2* | 5/2011 | Medo et al. | 435/6.1 |
| 7,951,410 B2 | 5/2011 | McMahon et al. | |
| 7,972,629 B2* | 7/2011 | Folan et al. | 424/535 |
| 7,998,501 B2* | 8/2011 | Singhal et al. | 424/439 |
| 8,278,046 B2* | 10/2012 | Medo et al. | 435/6.1 |
| 2001/0034614 A1 | 10/2001 | Fletcher-Haynes et al. | |
| 2001/0049096 A1 | 12/2001 | Brown | |
| 2002/0155445 A1 | 10/2002 | Jarvik | |
| 2002/0182243 A1 | 12/2002 | Medo | |
| 2003/0093171 A1 | 5/2003 | Soehnlen | |
| 2003/0152942 A1 | 8/2003 | Fors et al. | |
| 2003/0175358 A1* | 9/2003 | Euber et al. | 424/535 |
| 2003/0175701 A1 | 9/2003 | Griffiths et al. | |
| 2003/0213007 A1* | 11/2003 | Slattery et al. | 800/15 |
| 2003/0219812 A1 | 11/2003 | Quay et al. | |
| 2004/0181205 A1 | 9/2004 | Morton et al. | |
| 2004/0265462 A1 | 12/2004 | Carlson | |
| 2005/0042299 A1* | 2/2005 | Folan et al. | 424/535 |
| 2005/0053707 A1 | 3/2005 | Kopf et al. | |
| 2005/0096295 A1 | 5/2005 | McMahon et al. | |
| 2005/0100634 A1 | 5/2005 | Medo | |
| 2005/0175759 A1* | 8/2005 | Singhal | 426/590 |
| 2005/0214358 A1 | 9/2005 | Mikoshiba et al. | |
| 2005/0220894 A1 | 10/2005 | Williams et al. | |
| 2006/0115558 A1 | 6/2006 | Lamothe | |
| 2006/0204632 A1* | 9/2006 | Barrett-Reis et al. | 426/580 |
| 2006/0229256 A1* | 10/2006 | Anthony et al. | 514/19 |
| 2006/0233915 A1 | 10/2006 | Puski et al. | |
| 2007/0098863 A1 | 5/2007 | Medo et al. | |
| 2007/0104700 A1 | 5/2007 | Garcia-Rodenas et al. | |
| 2007/0196506 A2* | 8/2007 | Euber et al. | 424/535 |
| 2007/0203802 A1 | 8/2007 | Medo et al. | |
| 2007/0254062 A1* | 11/2007 | Singhal et al. | 426/2 |
| 2008/0118615 A1 | 5/2008 | Hartmann et al. | |
| 2008/0124430 A1 | 5/2008 | Medo et al. | |
| 2008/0187619 A1 | 8/2008 | Hartmann et al. | |
| 2008/0227101 A1 | 9/2008 | Medo et al. | |
| 2008/0254165 A1 | 10/2008 | Patel et al. | |
| 2008/0274230 A1 | 11/2008 | Johns et al. | |
| 2009/0175979 A1* | 7/2009 | Singhal et al. | 426/2 |
| 2009/0181848 A1 | 7/2009 | Lenz et al. | |
| 2009/0203592 A1 | 8/2009 | Beermann et al. | |
| 2009/0258121 A1 | 10/2009 | Medo | |
| 2010/0209526 A1* | 8/2010 | Folan et al. | 424/535 |
| 2010/0268658 A1 | 10/2010 | Medo et al. | |
| 2010/0280115 A1 | 11/2010 | Medo et al. | |
| 2011/0206684 A1 | 8/2011 | Medo | |
| 2011/0311689 A1 | 12/2011 | Medo et al. | |

FOREIGN PATENT DOCUMENTS

| | | |
|---|---|---|
| JP | 61-33895 U | 1/1986 |
| JP | 64-67141 A | 3/1989 |
| JP | 6-303900 A | 11/1994 |
| JP | 2002-532074 A | 10/2002 |
| JP | 2002-540806 A | 12/2002 |
| JP | 2005-525116 A | 8/2005 |
| SE | 380422 B | 11/1975 |
| WO | WO 98/57549 A1 | 12/1998 |
| WO | WO 00/43550 A2 | 7/2000 |
| WO | WO 2005/013709 A1 | 2/2005 |
| WO | WO 2005/051088 A2 | 6/2005 |
| WO | WO 2005/084129 A2 | 9/2005 |
| WO | WO 2006/026878 A1 | 3/2006 |
| WO | WO 2006/026879 A1 | 3/2006 |
| WO | WO 2007/035870 A2 | 3/2007 |
| WO | WO 2008/027572 A1 | 3/2008 |
| WO | WO 2008/067486 A2 | 6/2008 |
| WO | WO 2008/073888 A2 | 6/2008 |
| WO | WO 2010/030764 A2 | 3/2010 |

OTHER PUBLICATIONS

Burger and Schumm, "Detection of a Minor contributor in a DNA Sample Mixture from Human Milk," International Congress Series 1288:547-549 (2006).

Burger et al., "Detection of a 1% to 2% Contributor in a DNA Sample Mixture From Human Milk," International Society for Forensic Genetics 21$^{st}$ Congress Programme and Abstracts [online], Sep. 12-17, 2005 [retrieved on Mar. 26, 2007]. Retrieved from the Internet: http://www.ipatimup.pt/isfg2005/Programme.pdf; p. 75.

Carey et al., "Growth and phosphorus metabolism in premature infants fed human milk, fortified human milk, or special premature formula. Use of serum procollagen as a marker of growth," Am. J. Dis. Children 141(5):511-515 (1987).

Casey, "The nutritive and metabolic advantages of homologous milk," Proc. Nutr. Soc. 48:271-281 (1989).

Cowan et al., "Milk permeate as a dietary supplement for lactating dairy cows," Aus. J. Exp. Agric. 30(6):807-810 (1990).

Davies, D. P., "Adequacy of Expressed Breast Milk for Early Growth of Preterm Infants," Arch. Disease in Childhood. 1977. vol. 52, pp. 296-301.

Friis and Andersen, "Rate of inactivation of cytomegalovirus in raw banked milk during storage at—20° C. and pasteurisation," Br. Med. J. 285:1604-1605 (1982).

Fukushima et al., "Consumption of cow milk and egg by lactating women and the presence of β-lactoglobulin and ovalbumin in breast milk," Am. J. Clin. Nutr. 65:30-35 (1997).

Gartner et al., "Breastfeeding and the use of human milk," Pediatr. 115(2):496-506 (2005).

Geilman et al., "Production of an electrolyte beverage from milk permeate," J. Dairy Sci. 75(9):2364-2369 (1992).

Hagelberg S., et al., "Amino Acid Levels in the Critically Ill Preterm Infant Given Mother's Milk Fortified with Protein from Human or Cow's Milk" Acta Paediatr. Scand.1990. vol. 79, pp. 1163-1174.

Hagelberg, S., et al., "The Protein Tolerance of Very Low Birth Weight Infants Fed Human Milk Protein Enriched Mothers' Milk" Acta Paediatr. Scand. 1982. vol. 71, pp. 597-601.

Hartmann et al., "Best Practice Guidelines for the Operation of a Donor Human Milk Bank in an Australian NICU," Early Human Devel. 83:667-673 (2007).

Hylmö, P., et al., "Preparation of Fat and Protein from Banked Human Milk: Its Use in Feeding Very-Low-Birth-Weight Infants," Human Milk Banking, edited by A.F. Williams and J.D. Baum, Nestle Nutrition, Vewey/Raven Press, New York, 1984, pp. 55-61.

Itabashi et al., "Fortified preterm human milk for very low birth weight infants," Early Hum. Devel. 29:339-343 (1992).

Jenness and Palmer, "Substances Adsorbed on the Fat Globules in Cream and Their Relation to Churning. V. Composition of the 'Membrane' and Distribution of the Adsorbed Substances in Churning," J. Dairy Science 28(8):611-623 (1945).

Jensen et al., "Lipids in Human Milk and Infant Formulas," Ann. Rev. Nutr. 12:417-441 (1992).

Jensen et al., "Lipids of Bovine and Human Milks: A Comparison," J. Dairy Science 73:223-240 (1990).

Klein, Catherine J., "Nutrient Requirements for Preterm Infant Formulas," J. Nutr. 132:1395S-1577S, 2002.

Krukovsky et al., "The Effects of Nordihydroguaiaretic Acid, Salt, and Temperature of Storage on the Stability of Fat and Fat-Soluble Vitamins in Cream and Butter," J. Dairy Science 32(7):679-687 (1949).

Lapillione et al., "Mineral balance and whole body bone mineral content in very low-birth-weight infants," Acta Ped. 84(s405):117-122 (1994).

(56) References Cited

OTHER PUBLICATIONS

Lawrence, "Storage of human milk and the influence of procedures on immunological components of human milk," Acta Pædiatr. 88:14-18 (1999).

Lindblad B.S., et al., "Blood Levels of Critical Amino Acids in Very Low Birthweight Infants on a High Human Milk Protein Intake" Acta Paediatr. Scand.1982.vol. 296, pp. 24-27.

Lönnerdal, "Biochemistry and physiological function of human milk proteins," Am. J. Clin. Nutr. 42:1299-1317 (1985).

Lucas et al., "A human milk formula," Early Hum. Devel. 4/1:15-21 (1980).

Luck and Nau, "Nicotine and cotinine concentrations in the milk of smoking mothers: influence of cigarete consumption and diurnal variation," Eur J. Pediatr. 146:21-26 (1987).

McKiernan and Hull, "The Constituents of Neonatal Milk," Pediatr. Res. 16:60-64 (1982).

Melegh et al., "Changes of Plasma Free Amino Acids and Renal Clearances of Carnitines in Premature Infants During L-Carnitine-Supplemented Human Milk Feeding," J. Ped. Gastroenterol. Nutr. 7(3):424-429 (1998).

Moro et al., "Fortification of Human Milk: Evaluation of a Novel Fortification Scheme and of a New Fortifier," J. Ped. Gastroenterol. Nutr. 20:162-172 (1995).

Moro, G.E., et al., "Growth and Metabolic Responses in Low-Birth-Weight Infants Fed Human Milk Fortified with Human Milk Protein or with a Bovine Milk Protein Preparation," J. Pediatric Gastroenterol. and Nutr. 1991. vol. 13, pp. 150-154.

Ogundele, "Techniques for the storage of human breast milk: implications for anti-microbial functions and safety of stored milk," Eur. J. Pediatr. 159:793-797 (2000).

Panzer et al., "Immune thrombocytopenia in severe hemophilia A treated with high-dose intravenous immunoglobulin," Transfusion 26:69-72 (1986).

Polberger, S.K.T., "Fortified Human Milk for Very Low Birth Weight Infants: Effects on Growth and Metabolism," Dept. Pediatrics, University of Lund, Malmo 1990, pp. 1-148.

Polberger, S.K.T., et al., "Amino Acid Concentrations in Plasma and Urine in Very Low Birth Weight Infants Fed Non-Protein-Enriched or Human Milk Protein-Enriched Human Milk," Department of Pediatrics, University of Lund, Malmö General Hospital, S-21401 Malmö Sweden, pp. 131-148. Pediatrics 1990; 86: 909-915.

Polberger, S.K.T., et al., "Assessment of Eleven Different Plasma Proteins as Indicators of Protein Nutritional Status in Very Low Birth Weight Infants," Department of Pediatrics, University of Lund, Malmö General Hospital, S-21401 Malmö Sweden, 1990, pp. 115-129.

Polberger, S.K.T., et al., "Concentrations of Twelve Plasma Proteins at Birth in Very Low Birth Weight and in Term Infants," Department of Pediatrics, University of Lund, Malmö General Hospital, S-21401 Malmö Sweden, pp. 101-114. Acta Paediatr Scand. 1990; 79(8-9): 729-736.

Polberger, S.K.T., et al., "Growth of Very Low Birth Weight Infants on Varying Amounts of Human Milk Protein," Department of Pediatrics, University of Lund, Malmö General Hospital, S-21401 Malmö Sweden, pp. 69-87. Pediatr Res 1989; 25: 414-419.

Polberger, S.K.T., et al., "Urinary and Serum Urea as Indicators of Protein Metabolism in Very Low Birth Weight Infants Fed Varying Human Milk Protein Intakes," Department of Pediatrics, University of Lund, Malmö General Hospital, S-21401 Malmö Sweden, pp. 89-99. Acta Paediatr Scand. 1990; 79(8-9): 737-742.

Prentice, "Constituents of Human Milk," *Food and Nutrition Bulletin*, the United Nations University Press, 17(4), Dec. 1996. Retrieved from the internet: http://www.inffoundation.org/FNB/FNBIndexNEW.html.

Rönnholm, K., et al., "Supplementation with Human Milk Protein Improves Growth of Small Premature Infants Fed Human Milk," Pediatrics. 1986. vol. 77, No. 5, pp. 649-653.

Rönnholm, Kar., et al., "Human Milk Protein and Medium-Chain Triglyceride Oil Supplementation of Human Milk: Plasma Amino Acids in Very Low-Birth-Weight Infants," Pediatrics, American Academy of Pediatrics, Evanston, IL, vol. 74, No. 5, Jan. 1, 1984, pp. 792-799.

Saiki et al., "Genetic analysis of amplified DNA with immobilized sequence-specific oligonucleotide probes," Proc. Natl. Acad. Sci. USA 86:6230-6234 (1989).

Salle et al., "Effects of Calcium and Phosphorus Supplementation on Calcium retention and Fat Absorption in Preterm Infants Fed Pooled Human Milk," J. Ped. Gastroenterol. Nutr. 5(4):638-642 (1986).

Schanler et al., "Feeding strategies for premature infants: beneficial outcomes of feeding fortified human milk versus preterm formula," Pediatr. 103(6 Pt 1):1150-1157 (1999).

Schanler, R., et al., "Enhanced Fecal Excretion of Seleted Immune Factors in Very Low Birth Weight Infants Fed Fortified Human Milk," Pediatric Research. 1986. vol. 20, No. 8, pp. 711-715.

Schanler, R., et al., "Fortified mothers' milk for very low birth weight infants; results of growth and nutrient balance studies," J. Pediatrics. 1985. vol. 107, No. 3, pp. 437-444.

Schanler, R., et al., "Fortified mothers' milk for very low birth weight infants: results in macromineral balance studies," J. Pediatrics. 1985. vol. 107, No. 5, pp. 767-774.

Schanler, R., et al., "Mineral balance studies in very low birth weight infants fed human milk," J. Pediatrics. 1988. vol. 113, vol. 1, Part 2, pp. 230-238.

Srinivasan, L., et al., "Increased osmolality of breast milk with therapeutic additives," Arch. Dis. Child. Fetal. Neonatal Ed. 2004. 89:F514-F517.

Supplementary European Search Report mailed Apr. 20, 2011 in co-pending European application No. EP 07811645.6, 7 pages.

Supplementary European Search Report mailed Apr. 27, 2011 in co-pending European application No. EP 07864921.7, 8 pages.

Supplementary European Search Report mailed Mar. 24, 2009 in co-pending European application No. EP 06815100.0, 6 pages.

Supplementary European Search Report mailed Oct. 15, 2010 in co-pending European application No. EP 07865463.9, 6 pages.

Supplementary European Search Report mailed Oct. 29, 2012 in co-pending European application No. EP 09831061.8, 5 pages.

Terpstra, et al., "Antimicrobial and Antiviral Effect of High-Temperature Short-Time (HTST) Pasteurization Applied to Human Milk," Breastfeeding Med. 2007. vol. 2, pp. 27-33.

The Dairy Council, "The Nutritional Composition of Dairy Products," pp. 1-49, 2002.

Tully, "Is Pasteurized Mother's Own or Donor Milk an Answer to the HIV Crisis," J. Hum. Lact. 15(4):345-346 (1999).

Virus Safety Services, Sanquin Research, Final Report FR4500, "Process Validation Breast Milk Step 1 for Inactivation of BVDV/HAV/HIV/PSR," May 27, 2002. pp. 1-33.

Voyer, M., et al. "Human Milk Lacto-Engineering," Acta Paediatr. Scand. 1984. vol. 73, pp. 302-306.

Williams et al., "Human Milk Banking," J. Trop. Pediatr. 31:185-190 (1985).

Young, "International Search Report," and "Written Opinion of the International Searching Authority," 11 pages, from International Patent Application No. PCT/US09/66430, United States Patent and Trademark Office, Alexandria, Virginia, USA (mailed Jan. 26, 2010).

Young, "International Search Report," and "Written Opinion of the International Searching Authority," 6 pages, from International Patent Application No. PCT/US07/19234, United States Patent and Trademark Office, Alexandria, Virginia, USA (mailed Jan. 18, 2008).

Young, "International Search Report," and "Written Opinion of the International Searching Authority," 8 pages, from International Patent Application No. PCT/US07/86973, United States Patent and Trademark Office, Alexandria, Virginia, USA (mailed May 5, 2008).

Young, "International Search Report," and "Written Opinion of the International Searching Authority," 8 pages, from International Patent Application No. PCT/US07/85969, United States Patent and Trademark Office, Alexandria, Virginia, USA (mailed May 8, 2008).

Young, "International Search Report," and "Written Opinion of the International Searching Authority," 8 pages, from International Patent Application No. PCT/US06/36827, United States Patent and Trademark Office, Alexandria, Virginia, USA (mailed Sep. 5, 2007).

* cited by examiner

METHODS FOR TESTING MILK

CROSS REFERENCE TO RELATED APPLICATIONS

This application is a continuation of U.S. application Ser. No. 13/079,932, filed Apr. 5, 2011, now U.S. Pat. No. 8,278,046, which is a continuation of U.S. application Ser. No. 12/052,253, filed Mar. 20, 2008, now U.S. Pat. No. 7,943,315, which is a continuation-in-part and claims priority to the international application PCT/US2006/036827 with an international filing date of Sep. 20, 2006, which, in turn, claims priority under 35 U.S.C. §119 from Provisional Application Ser. Nos. 60/719,317, filed Sep. 20, 2005, and 60/731,428, filed Oct. 28, 2005. The disclosures of all of each of which are incorporated herein by reference in their entireties.

TECHNICAL FIELD

The methods featured herein are related generally to methods of testing mammary fluid (including milk) to establish or confirm the identity of the donor of the mammary fluid.

BACKGROUND

Unlike blood donors, who give their donation under the direct supervision of the blood bank personnel, human breast milk donors tend to pump their milk for donation at home or other locations convenient to them and then often store the breast milk in their freezers until they have accumulated enough to bring to the donation center. Thus, in the absence of direct supervision of the donations, questions may arise as to the provenance of the donated breast milk.

In order to establish that the breast milk provided by a donor is, in fact, exclusively from that human female donor, some form of testing to establish donor identity should occur.

Many different methods of DNA typing are known for identifying or typing specimens from humans. Such methods include short tandem repeats ("STR"), microsatellite repeats or simple sequence repeats ("SSR") analysis of human DNA; analysis of multiple human genes and analysis of human lymphocyte antigen (HLA) genes and loci by polymerase chain reaction (PCR) analysis, restriction length polymorphism analysis and other methods.

It is known that humans possess antigens which are specific to that individual. For example, the human leukocyte antigens (HLA) have been used in the past for typing tissue for transplantation.

Such typing methods, among others, can be used to test for donor identity in the methods featured herein.

SUMMARY

The methods and systems featured herein relate to diagnosing or screening mammary fluid from any number of mammalian organisms. In one aspect, the invention provides methods and systems for diagnosing or screening human milk samples to confirm that the milk is from a defined source.

The methods include obtaining a donated reference sample from a potential mammary fluid donor, e.g., a human breast milk donor. The sample can be analyzed at or around the time of obtaining the sample for one or more markers that can identify the potential donor. Alternatively, or in addition, the sample can be stored and analyzed for identifying markers at a later time. When the potential mammary fluid donor expresses the mammary fluid and donates the fluid (e.g., by bringing or sending the fluid to the donation center), the mammary fluid can be analyzed for the same marker or markers as the donor's reference sample. The match between the markers (and lack of any additional unmatched markers) would indicate that the donated milk comes from the same individual as the one who donated the reference sample. Lack of a match (or presence of additional unmatched markers) would indicate that the donated mammary fluid either comes from a non-tested donor or has been contaminated with fluid from a non-tested donor.

The testing of the reference sample and of the donated mammary fluid can be carried out at the donation facility and/or milk processing facility. The results of the reference sample tests can be stored and compared against any future donations by the same donor.

Testing donors to confirm their identity improves safety of donated milk. It ensures the provenance of the donated milk, which as discussed above, is most often donated without supervision by the donor center. Testing donor identity by the methods featured herein allows for multiple donations by the same donor, whose identity can be confirmed at the time of each donation. The donor can live at any distance from the donation and/or processing facilities, as she can send her milk at long distances, and her identity can be confirmed based on reference samples or reference tests stored at the donation and/or processing facility.

The mammary fluid tested by the methods featured herein can be processed for further use. The donation facility and milk processing facility can be the same or different facility. The donated milk can be processed, e.g., to obtain human milk fortifiers, standardized human milk formulations; human lipid products, and/or compositions for total parenteral nutrition.

In one aspect, a method of determining whether a donated mammary fluid was obtained from a specific subject is featured. The method includes: (a) testing a donated biological sample from the specific subject to obtain at least one reference identity marker profile for at least one marker; (b) testing a sample of the donated mammary fluid to obtain at least one identity marker profile for the at least one marker in step (a); and (c) comparing the identity marker profiles, wherein a match between the identity marker profiles indicates that the mammary fluid was obtained from the specific subject.

Embodiments can include one or more of the following features.

The method can further include: (d) processing the donated mammary fluid whose identity marker profile has been matched with a reference identity marker profile. The mammary fluid is human breast milk. Processing can include generating a pasteurized milk composition for administration to a human infant. The processing can include: filtering the milk; heat-treating the milk; separating the milk into cream and skim; adding a portion of the cream to the skim; and pasteurizing.

The processed and pasteurized milk composition can include: a human protein constituent of about 35-85 mg/mL; a human fat constituent of about 60-110 mg/mL; and a human carbohydrate constituent of about 60-140 mg/mL, and optionally, one or more constituents selected from the group consisting of: calcium, chloride, copper, iron, magnesium, manganese, phosphorus, potassium, sodium, and zinc.

The processed and pasteurized milk composition can include: a human protein constituent of about 11-20 mg/mL; a human fat constituent of about 35-55 mg/mL; and a human carbohydrate constituent of about 70-120 mg/mL, and, optionally, one or more components selected from the group consisting of: calcium, chloride, copper, iron, magnesium, manganese, phosphorus, potassium, sodium, and zinc.

The processing can include separating the milk into a cream portion and a skim portion, processing the cream portion, and pasteurizing the cream portion.

The testing of the mammary fluid sample and the testing of the biological sample can include a nucleic acid typing, e.g., STR analysis, HLA analysis, multiple gene analysis, and a combination thereof.

The donated mammary fluid can be frozen, and the method can include obtaining the mammary fluid sample by drilling a core through the frozen fluid. Alternatively, or in addition, the method can include obtaining the mammary fluid sample by scraping the surface of the frozen mammary fluid.

The method can further include isolating the mammary fluid prior to step (b).

The mammary fluid sample can include a mixture of one or more mammary fluid samples. The testing of the mammary fluid sample and the testing of the biological sample can include antibody testing to obtain a self-antigen profile. The sample of the donated mammary fluid can include a selected solid fraction of the fluid. The identity profiles can include peptide markers. The donated biological sample can be, e.g., milk, saliva, buccal cell, hair root, and blood.

A lack of a match between the identity marker profiles indicates contamination of the mammary fluid by another mammal.

Steps (a) through (c) can be carried out at a human breast milk donation center or at a milk processing facility.

In another aspect the disclosure is related to a method for determining whether breast milk was obtained from a specific human comprising testing a sample of the breast milk to obtain an identity marker profile and testing a biological sample from the human to obtain a reference identity marker profile and comparing the identity marker profiles.

The disclosure provides a method for determining whether breast milk was obtained from a desired source or specific human comprising nucleic acid typing of a sample of the breast milk to obtain a DNA type profile and nucleic acid typing of a biological sample from the human to obtain a reference DNA type profile and comparing the DNA type profiles.

In one embodiment, the method of nucleic acid typing of the biological sample from the human is selected from STR analysis, HLA analysis or multiple gene analysis. It is further contemplated that nucleic acid typing method used for the breast milk sample is the same as that used for the biological sample. It is contemplated that the loci/alleles used for the DNA type profile will be the same for both the reference DNA type profile and the breast milk sample DNA type profile.

In one embodiment the breast milk will be frozen. It is further contemplated that the method for obtaining the breast milk sample from the frozen breast milk will be by drilling a core through the frozen breast milk. Alternatively, it is contemplated that the breast milk sample may be obtained by scraping the surface of the frozen breast milk.

In another embodiment the breast milk will be liquid. It is contemplated that the method for obtaining the breast milk sample will be by isolating the breast milk sample by pipette or other means.

In another embodiment the breast milk samples may be combined or mixed prior to nucleic acid typing.

The disclosure also provides a method for determining whether breast milk was obtained from a defined source (e.g., a specific human) comprising testing of a sample of the breast milk to obtain a self-antigen profile and testing a biological sample from the human to obtain a reference self-antigen profile and comparing the self-antigen profiles.

The disclosure also provides an article of manufacture or kit comprising a container, a label on the container and a reagent for detecting or measuring identity markers, wherein the label on the container indicates that the reagent can be used to determine the identity marker profile of breast milk. In one embodiment, the reagent comprises PCR materials (a set of primers, DNA polymerase and 4 nucleoside triphosphates) that hybridize with the gene or loci thereof. The kit may further comprise additional components, such as reagents, for detecting or measuring the detectable entity or providing a control. Other reagents used for hybridization, prehybridization, DNA extraction, visualization and the like may also be included, if desired. In another embodiment, the regent is an antibody for detecting self-antigens.

Unless defined otherwise, technical and scientific terms used herein have the same meaning as commonly understood by one of skill in the art to which this invention belongs.

One skilled in the art will recognize many methods and materials similar or equivalent to those described herein, which could be used in the practice of this invention. Indeed, the invention is no way limited to the methods and materials described herein. For purposes of the methods featured herein, the following terms are defined.

"Mammary fluid" includes breast milk and/or colostrum expressed from lactating female subjects. Whole mammary fluid, selected liquid or solid fractions of the mammary fluid, whole cells or cellular constituents, proteins, glycoproteins, peptides, nucleotides (including DNA and RNA polynucleotides) and other like biochemical and molecular constituents of the mammary fluid can be used in the present methods. The mammary fluid may be obtained from any number of species of female subjects including, but not limited to, humans, bovines, goats and the like.

"Identity marker" includes a marker that can be used to identify an individual subject from other subjects in a population. Such markers are present in the cells found in mammary fluid. Such markers could include, but are not limited to, genes, alleles, loci, antigens polypeptides or peptides.

An "identity marker profile" comprises a profile of a number of identity markers. The profile identifies the individual human or subject from other humans with a sufficient degree of certainty. It is contemplated that the identity marker profile identifies at least one human from 100,000 humans, or 1 human from 1 million humans or 1 human from 5 million humans.

"Nucleic acid typing" refers to a method of determining the DNA type profile of a biological or milk sample. Such methods include, but are not limited to: STR analysis, HLA analysis or multiple gene analysis of genes/alleles/loci present in a polynucleotide sample of the biological or milk sample.

"DNA type profile" refers to a profile of a human's or subject's genomic DNA, which is sufficient to distinguish the individual human or subject from other humans with a sufficient degree of certainty. It is contemplated that the DNA profile identifies at least one human from 100,000 humans, or 1 human from 1 million humans or 1 human from 5 million humans. Generally the methods featured herein involve identifying alleles of at least 5 loci/genes or at least 10 loci/genes or at least 13 loci/gene.

An "allele" comprises one of the different nucleic acid sequences of a gene at a particular locus on a chromosome. One or more genetic differences can constitute an allele. Examples of HLA allele sequences are set out in Mason and Parham (1998) *Tissue Antigens* 51:417-66, which list HLA-A, HLA-B, and HLA-C alleles and Marsh et al (1992); and *Hum. Immunol.* 35:1, which list MLA Class II alleles for DRA, DRB, DQA1, DQB1, DPA1, and DPB1.

A "locus" comprises a discrete location on a chromosome. The loci may be part of a gene or part of repeat sequence. Exemplary human leukocyte antigens (HLAs) loci are the class I MHC genes designated HLA-A, HLA-B and HLA-C; nonclassical class I genes including HLA-E, HLA-F, HLA-G, HLA-H, HLA-J and HLA-X, MIC; and class II genes such as HLA-DP, HLA-DQ and HLA-DR. Exemplary STR loci are: CSF1PO, D3S1358, D5S818, D7S820, D8S1179, D13S317, D16S539, DI8S51, D21S11, DYS19, F13A1, FES/FPS, FGA, HPRTB, THO1, TPOX, DYS388, DYS391, DYS392, DYS393, D2S1391, D18S535, D2S.1338, D19S433, D6S477, D1S518, D14S306, D22S684, F13B, CD4, D12S391, D10S220 and D7S523 (see, e.g., U.S. Pat. No. 6,090,558).

A method of HLA analysis or human leukocyte antigen analysis is a method that permits the determination or assignment of one or more genetically distinct human leukocyte antigen (HLA) genetic polymorphisms by any number of methods known in the art. Some methods contemplated are described below.

A method of STR analysis is a method that permits the determination or assignment of one or more genetically distinct STR genetic polymorphisms by any number of methods known in the art. Some methods contemplated are described herein.

A method of multiple gene analysis is a method that permits the determination or assignment of one or more genetically distinct genetic polymorphisms of human genes by any number of methods known in the art. Such genes may or may not include the HLA genes. Some methods contemplated are described herein.

A number of amplification techniques are known in the art. Amplifying refers to a reaction wherein a template nucleic acid, or portions thereof, is duplicated at least once. Such amplification techniques include arithmetic, logarithmic, or exponential amplification. The amplification of a nucleic acid can take place using any nucleic acid amplification system, both isothermal and thermal gradient based including, but not limited to, polymerase chain reaction (PCR), reverse-transcription-polymerase chain reaction (RT-PCR), ligase chain reaction (LCR), self-sustained sequence reaction (3SR), and transcription mediated amplifications (TMA). Typical nucleic acid amplification mixtures (e.g., PCR reaction mixture) include a nucleic acid template that is to be amplified, a nucleic acid polymerase, nucleic acid primer sequence(s), nucleotide triphosphates, and a buffer containing all of the ion species required for the amplification reaction.

Amplification products obtained from an amplification reaction typically comprise a single stranded or double stranded DNA or RNA or any other nucleic acid products of isothermal and thermal gradient amplification reactions that include PCR, LCR, and the like.

A "template nucleic acid" refers to a nucleic acid polymer that is sought to be copied or amplified. The template nucleic acid(s) can be isolated or purified from a cell, tissue, and the like. The template nucleic acid can comprise genomic DNA, cDNA, RNA, or the like.

Primers are used in some amplification techniques. A primer comprises an oligonucleotide used in an amplification reaction (e.g., PCR) to amplify a target nucleic acid. The primer is typically single stranded. The primer may be from about 5 to 30 nucleic acids in length, more commonly from about 10 to 25 nucleic acids in length.

An STR locus-specific primer is an oligonucleotide that hybridizes to a nucleic acid target variant that defines or partially defines that particular STR locus.

An HLA allele-specific primer is an oligonucleotide that hybridizes to a nucleic acid target variant that defines or partially defines that particular HLA allele.

HLA locus-specific primer is an oligonucleotide that permits the amplification of an HLA locus or that can hybridize specifically to an HLA locus.

An allele-specific primer is an oligonucleotide that hybridizes to a target nucleic acid variant that defines or partially defines that particular gene allele.

A locus-specific primer is an oligonucleotide that permits the amplification of a gene locus or that can hybridize specifically to a gene locus.

A forward primer and a reverse primer constitute a pair of primers that can bind to a template nucleic acid and under proper amplification conditions produce an amplification product. If the forward primer is binding to the sense strand then the reverse primer is binding to antisense strand. Alternatively, if the forward primer is binding to the antisense strand then the reverse primer is binding to sense strand. In essence, the forward or reverse primer can bind to either strand so long as the other reverse or forward primer binds to the opposite strand.

Any number of detectable labels can be used to detect a target nucleic acid by use of amplification or other techniques. A detectable label refers to a moiety that is attached through covalent or non-covalent techniques to an oligonucleotide or other detection agent. Examples of detectable labels include a radioactive moiety, a fluorescent moiety, a chemiluminescent moiety, a chromogenic moiety and the like. Fluorescent moieties comprise chemical entities that accepts radiant energy of one wavelength and emits radiant energy at a second wavelength.

Various hybridization techniques can be used in the methods described herein. Hybridizing or hybridization refers to the binding or duplexing of a molecule to a substantially complementary polynucleotide or fragment through bonding via base pairing. Hybridization typically involves the formation of hydrogen bonds between nucleotides in one nucleic acid and a complementary second nucleic acid. Methods of hybridization can include highly stringent, moderately stringent, or low stringency conditions.

The term "stringent conditions" refers to conditions under which a capture oligonucleotide, oligonucleotide or amplification product will hybridize to its target nucleic acid. "Stringent hybridization conditions" or "highly stringent conditions" are sequence dependent and will be different with different environmental parameters (e.g., salt concentrations, and presence of organics). Generally, stringent conditions are selected to be about 5° C. to 20° C. lower than the thermal melting point ($T_m$) for a specific nucleic acid at a defined ionic strength and pH. Stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid hybridizes to a matched probe. Longer oligonucleotides hybridize at higher temperatures. Typically, stringent conditions will be those in which the salt concentration comprises about 0.01 to 1.0 M Na (or other salts) at pH 7.0 to 8.3 and the temperature is at least about 300 C for short probes (e.g., 10 to 50 nucleotides). Stringent conditions may also be achieved with the addition of destabilizing agents such as formamide. An extensive guide to the hybridization and washing of nucleic acids is found in Tijssen (1993) *Laboratory Techniques in Biochemistry and Molecular Biology—Hybridization with Nucleic Acid Probes* parts I and II, Elsevier, N.Y.; Choo (ed) (1994) *Methods Molecular Biology* Volume 33, *In Situ Hybridization Protocols*, Humana Press Inc., New Jersey; Sambrook et al., *Molecular Cloning, A Laboratory Manual* (2nd ed. 1989); *Current Protocols in Molecular Biology*, Ausubel et al., eds., (1994).

Hybridization conditions for a particular probe, primer and target are readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of single stranded nucleic acids to anneal with a complementary strands present in an environment below their inciting temperature. The higher the degree of desired homology between a probe and hybridizable target, the higher the relative temperature which can be used. As a result, it follows that higher relative temperatures would tend to make the reaction conditions more stringent, while lower temperatures less so.

Hybridization wash conditions are ordinarily determined empirically for hybridization of each probe or set of primers to a corresponding target nucleic acid. The target nucleic acid and probes/primers are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C. more usually in excess of about 37° C., and occasionally in excess of about 45° C. Stringent salt conditions will ordinarily be less than about 1000 mM, usually less than about 500 mM, more usually less than about 400 mM, typically less than about 300 mM, typically less than about 200 mM, and more typically less than about 150 mM. However, the combination of parameters is more important than the measure of any single parameter. See, e.g., Wetmur et al., *J. Mol Biol* 31:349-70 (1966), and Wetmur, *Critical Reviews Biochemistry and Molecular Biology* 26 (34):227-59 (1991).

In one embodiment, highly stringent conditions comprise hybridization in 50% formamide, 6×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (100/µg/ml), 0.5% SDS, and 10% dextran sulfate at 420 C, with washes at 42° C. in 2×SSC (sodium chloride/sodium citrate) and 0.1% SDS, followed by a high-stringency wash comprising of 0.2×SSC containing 0.1% SDS at 42° C.

The terms "complement," "complementarity" or "complementary," as used herein, are used to describe single-stranded polynucleotides related by the rules of antiparallel base-pairing. For example, the sequence 5'-CTAGT-3' is completely complementary to the sequence 5'-ACTAG-3'. Complementarity may be "partial," where the base pairing is less than 100%, or complementarity may be "complete" or "total," implying perfect 100% antiparallel complementation between two polynucleotides. By convention in the art, single-stranded nucleic acid molecules are written with their 5' ends to the left, and their 3' ends to the right.

The term "complementary base pair" refers to a pair of bases (nucleotides) each in a separate nucleic acid in which each base of the pair is hydrogen bonded to the other. A "classical" (Watson-Crick) base pair contains one purine and one pyrimidine; adenine pairs specifically with thymine (A-T), guanine with cytosine (G-C), uracil with adenine (U-A). The two bases in a classical base pair are said to be complementary to each other.

"Substantially complementary" between a probe or primer nucleic acid and a target nucleic acid embraces minor mismatches that can be accommodated by reducing the stringency of the hybridization media to achieve the desired degree of hybridization and identification of hybridized target polynucleotides.

A "capture oligonucleotide" useful for identification of a target nucleic acid refers to a nucleic acid or fragment that can hybridize to a polynucleotide, oligonucleotide, amplification product, or the like, and has the ability to be immobilized to a solid phase. A capture oligonucleotide typically hybridizes to at least a portion of an amplification product containing complementary sequences under stringent conditions.

An "HLA locus-specific capture oligonucleotide" is a capture oligonucleotide that is complementary to and hybridizes to a conserved region of an HLA locus. For example, the capture oligonucleotide can be specific for the HLA-A locus and will hybridize to one or more conserved regions or subsequences of the HLA-A locus.

Similarly, an "STR locus-specific capture oligonucleotide" is a capture oligonucleotide that is complementary to and hybridizes to a conserved region of an STR locus. A locus-specific capture oligonucleotide is a capture oligonucleotide that is complementary to and hybridizes to a conserved region of a genetic locus.

A capture oligonucleotide is typically immobilized on a solid phase directly or indirectly. Such immobilization may be through covalent and/or non-covalent bonds.

The term "amplicon", is used herein to mean a population of DNA molecules that has been produced by amplification, e.g., by PCR.

The term "subject" refers to a lactating mammalian subject. The subject may be a human, bovine, goat and the like. For example, the screening as to the origination of milk products from non-human mammals may be important for the tracing of products to a particular bovine, for example, for FDA or other purposes.

"Mutation" as used herein sometimes refers to a functional polymorphism that occurs in the population, and is strongly correlated to a gene. "Mutation" is also used herein to refer to a specific site and type of functional polymorphism, without reference to the degree of risk that particular mutation poses to an individual for a particular disease.

A "self-antigen" is an antigen which identifies the individual subject from other subjects in the population. Exemplary self-antigens include the major histocompatibility antigens (MHC) antigens or the blood type antigens (ABO).

A "self antigen profile" means a profile of a human's or subject's self-antigens which is sufficient to distinguish the individual subject from other subjects with a sufficient degree of certainty.

The term "antibody" is used in its broadest sense and covers polyclonal antibodies, monoclonal antibodies, single chain antibodies and antibody fragments.

The details of one or more embodiments of the methods featured herein are set forth in the description below. Other features, objects, and advantages of the methods will be apparent from the description and the claims.

All patents, patent applications, and references cited herein are incorporated in their entireties by reference.

DETAILED DESCRIPTION

In one aspect, the methods featured herein are used to determine milk origination. For example, in order to ensure that human breast milk received from a specific human actually comes from that human, methods of identity testing are needed on samples of milk received from each human. Testing donors to confirm their identity improves safety of donated milk. It ensures the provenance of the donated milk, which as discussed above, is most often donated without supervision of personnel of the organization that will be receiving the milk, e.g., a milk bank center. Testing donor identity by the methods featured herein allows for multiple donations by the same donor, whose identity can be confirmed at the time of each donation. The donor can live at any distance from the donation and/or processing facilities, as she can send her milk at long distances, and her identity can be confirmed based on reference samples or reference test results stored at the donation and/or processing facility.

As part of the qualification process for donating milk, each potential milk donor will be identified by biological methods (e.g., biological fingerprinting, as described herein). The identifying characteristics of the individual (i.e., at least one identity marker) will also be present in the donor's milk. Such characteristics will be used to match the donated milk with a specific donor.

Obtaining a Reference Biological Sample

The methods featured herein include, inter alia, obtaining at least one donated reference sample from a potential mammary fluid donor, e.g., a human breast milk donor. Such sample may be obtained by methods known in the art such as, but not limited to, a cheek swab sample of cells, or a drawn blood sample, milk, saliva, hair roots, or other convenient tissue. Samples of reference donor nucleic acids (e.g., genomic DNA) can be isolated from any convenient biological sample including, but not limited to, milk, saliva, buccal cells, hair roots, blood, and any other suitable cell or tissue sample with intact interphase nuclei or metaphase cells. The sample is labeled with a unique reference number. The sample can be analyzed at or around the time of obtaining the sample for one or more markers that can identify the potential donor. Results of the analysis can be stored, e.g., on a computer-readable medium. Alternatively, or in addition, the sample can be stored and analyzed for identifying markers at a later time.

It is contemplated that the biological reference sample may be DNA typed by methods known in the art such as STR analysis of STR loci, HLA analysis of HLA loci or multiple gene analysis of individual genes/alleles (further discussed below). The DNA-type profile of the reference sample is recorded and stored, e.g., on a computer-readable medium.

It is further contemplated that the biological reference sample may be tested for self-antigens using antibodies known in the art or other methods to determine a self-antigen profile. The antigen (or another peptide) profile can be recorded and stored, e.g., on a computer-readable medium.

Testing a Sample of Donated Mammary Fluid

A subject desiring to donate mammary fluid will express the mammary fluid (breast milk) using standard procedures. The mammary fluid is typically collected in containers useful for shipping and storage. The mammary fluid can be frozen prior to donation. The mammary fluid may be frozen at the donation facility or processing facility for later analysis and use or analyzed without freezing. One or more of the containers with donated fluid can be used for obtaining a test sample. The test sample is taken for identification of one or more identity markers.

Methods of obtaining a sample of expressed frozen fluid include a stainless steel boring tool used to drill a core the entire length of the container. Alternatively, a sample may be scraped from the surface of the frozen mammary fluid. The container may contain a separate portion for collection of a sample of the expressed mammary fluid, and this portion may be removed as the sample for testing. Where the mammary fluid is in liquid form it is contemplated that the method for obtaining the test sample will be by pipette or other means.

A sample of the donated mammary fluid is analyzed for the same marker or markers as the donor's reference sample. The marker profiles of the reference biological sample and of the donated mammary fluid are compared. The match between the markers (and lack of any additional unmatched markers) would indicate that the donated milk comes from the same individual as the one who donated the reference sample. Lack of a match (or presence of additional unmatched markers) would indicate that the donated mammary fluid either comes from a non-tested donor or has been contaminated with fluid from a non-tested donor.

The donated mammary fluid sample and the donated reference biological sample can be tested for more than one marker. For example, each sample can be tested for multiple DNA markers and/or peptide markers. Both samples, however, need to be tested for at least some of the same markers in order to compare the markers from each sample.

Thus, the reference sample and the donated mammary fluid sample may be tested for the presence of differing identity marker profiles. If there are no identity marker profiles other than the identity marker profile from the expected subject, it generally indicates that there was no fluid (e.g., milk) from other humans or animals contaminating the donated mammary fluid. If there are signals other than the expected signal for that subject, the results are indicative of contamination. Such contamination will result in the mammary fluid (e.g., milk) failing the testing.

The testing of the reference sample and of the donated mammary fluid can be carried out at the donation facility and/or milk processing facility. The results of the reference sample tests can be stored and compared against any future donations by the same donor.

It is contemplated that samples from a number of milk containers from the same subject may be pooled for identity marker testing. It is contemplated that at least 2 samples, at least 5 samples or at least 8 samples may be pooled for testing.

It is contemplated that the test sample of the donated mammary fluid may be tested by nucleic acid typing using methods known in the art, such as, STR analysis of STR loci, HLA analysis of HLA loci or multiple gene analysis of individual genes/alleles to obtain the DNA-type of the milk sample. The donated mammary fluid can also be tested for peptide profiles, e.g., antigen profile.

The DNA-type or another biological profile (i.e., identity profile (s)) of the donated mammary fluid test sample (s) will be compared to the reference DNA-type or another biological profile for the putative donor. A match or identity of the DNA-type or biological profile will indicate that the mammary fluid was obtained from a same (i.e., a specified subject).

Use of the Donated and Tested Mammary Fluid

The mammary fluid tested by the methods featured herein can be processed for further use. The donation facility and milk processing facility can be the same or different facility. The donated milk whose provenance has been confirmed can be processed, e.g., to obtain human milk fortifiers, standardized human milk formulations, and/or human lipid compositions. As discussed above, testing the mammary fluid to confirm the identity of the donor ensures safety of the mammary fluid and any products derived from such fluid.

Processing of human milk to obtain human milk fortifiers (e.g., PROLACTPLUS™ Human Milk Fortifiers, e.g., PROLACT+4™, PROLACT+6™, PROLACT+8™, and/or PROLACT+10™, which are produced from human milk and contain various concentrations of nutritional components) and the compositions of the fortifiers are described in U.S. patent application Ser. No. 11/947,580, filed on Nov. 29, 2007, the contents of which are incorporated herein in their entirety. These fortifiers can be added to the milk of a nursing mother to provide an optimal nutritional content of the milk for, e.g., a preterm infant. Depending on the content of mother's own milk, various concentrations of the fortifiers can be added to mother's milk.

Methods of obtaining standardized human milk formulations (exemplified by PROLACT20™, NEO20™, and/or PROLACT24) and formulations themselves are also discussed in U.S. patent application Ser. No. 11/947,580, filed on Nov. 29, 2007, the contents of which are incorporated herein in their entirety. These standardized human milk formulations can be used to feed, e.g., preterm infants, without mixing them with other fortifiers or mills. They provide a nutritional human-derived formulation and can substitute for mother's milk.

Compositions that include lipids from human milk, methods of obtaining such compositions, and methods of using such compositions to provide nutrition to patients are described in PCT Application PCT/US07/86973 filed on Dec. 10, 2007, the contents of which are incorporated herein in their entirety.

Methods of obtaining other nutritional compositions from human milk that can be used with the methods featured herein are discussed in U.S. patent application Ser. No. 11/012,611, filed on Dec. 14, 2004, and published as U.S. 2005/0100634 on May 12, 2005, the contents of which are incorporated herein in their entirety.

Processing of milk that has been tested with the methods featured herein can be carried out with large volumes of donor milk, e.g., about 75 liters/lot to about 2,000 liters/lot of starting material.

The methods featured herein can also be integrated with methods of facilitating collection and distribution of human milk over a computer network, e.g., as described in U.S. patent application Ser. No. 11/526,127, filed on Sep. 22, 2006, and published as U.S. 2007/0098863 on May 3, 2007; and in U.S. patent application Ser. No. 11/679,546, filed on Feb. 27, 2007, and published as U.S. 2007/0203802 on Aug. 30, 2007. The contents of both applications are incorporated herein in their entireties.

Nucleic Acid Identity Marker Profiles

As discussed above, samples of reference donor nucleic acids (e.g., genomic DNA) are isolated from any convenient biological sample including, but not limited to, milk, saliva, buccal cells, hair roots, blood, and any other suitable cell or tissue sample with intact interphase nuclei or metaphase cells.

Methods for isolation of nucleic acids (e.g., genomic DNA) from these various sources are described in, for example, Kirby, DNA Fingerprinting, An Introduction, W. H. Freeman & Co. New York (1992). Nucleic acids (e.g., genomic DNA) can also be isolated from cultured primary or secondary cell cultures or from transformed cell lines derived from any of the aforementioned tissue samples.

Samples of RNA can also be used. RNA can be isolated as described in Sambrook et al., supra, RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that PCR indirectly amplifies a specific population of RNA transcripts. See, e.g., Sambrook et al., supra, and Berg et al., *Hum. Genet.* 85:655-658 (1990).

Short tandem repeat (STR) DNA markers, also referred to as microsatellites or simple sequence repeats (SSRs) or DNA tandem nucleotide repeat ("DTNR"), comprise tandem repeated DNA sequences with a core repeat of 2-6 base pairs (bp). STR markers are readily amplified during PCR by using primers that bind in conserved regions of the genome flanking the repeat region.

Commonly sized repeats include dinucleotides, trinucleotides, tetranucleotides and larger. The number of repeats occurring at a particular genetic locus varies from a few to hundreds depending on the locus and the individual. The sequence and base composition of repeats can vary significantly, including a lack of consistency within a particular nucleotide repeat locus. Thousands of STR loci have been identified in the human genome and have been predicted to occur as frequently as once every 15 kb. Population studies have been undertaken on dozens of these STR markers as well as extensive validation studies in forensic laboratories. Specific primer sequences located in the regions flanking the DNA tandem repeat region have been used to amplify alleles from STR loci via the polymerase chain reaction ("PCR"). The PCR products include the polymorphic repeat regions, which vary in length depending on the number of repeats or partial repeats, and the flanking regions, which are typically of constant length and sequence between samples.

The number of repeats present for a particular individual at a particular locus is described as the allele value for the locus. Because most chromosomes are present in pairs, PCR amplifications of a single locus commonly yields two different sized PCR products representing two different repeat numbers or allele values. The range of possible repeat numbers for a given locus, determined through experimental sampling of the population, is defined as the allele range, and may vary for each locus, e.g., 7 to 15 alleles. The allele PCR product size range (allele size range) for a given locus is defined by the placement of the two PCR primers relative to the repeat region and the allele range. The sequences in regions flanking each locus must be fairly conserved in order for the primers to anneal effectively and initiate PCR amplification. For purposes of genetic analysis di-, tri-, and tetranucleotide repeats in the range of 5 to 50 are typically utilized in screens. Forensic laboratories use tetranucleotide loci (i.e., 4 bp in the repeat) due to the lower amount of "stutter" produced during PCR (Stutter products are additional peaks that can complicate the interpretation of DNA mixtures by appearing in front of regular allele peaks). The number of repeats can vary from 3 or 4 repeats to more than 50 repeats with extremely polymorphic markers. The number of repeats and hence the size of the PCR product, may vary among samples in a population making STR markers useful in identity testing of genetic mapping studies.

There are 13 core STR loci identified in the United States CODIS database. These STR loci are THO1, TPOX, CSF1PO, VWA, FGA, D3S1358, D5S818, D7S820, D13S317, D16S539, D8S1179, D18S51 and D21S11. The sex-typing marker amelogenin, is also included in the STR multiplexes that cover the 13 core STR loci. The 13 CODIS STR loci are covered by the Profiler Plus™ and COfiler™ kits from Applied Biosystems (ABI) (Foster City, Calif.). It is contemplated that the following STR loci may be used in this invention: CSF1PO, D3S1358, D5S818, D7S820, D8S1179, D13S317, D16S539, D18S51, D21S11, DYS19, F13A1, FESfFPS, FGA, HPRTB, THO1, TPOX, DYS388, DYS391, DYS392, DYS393, D2S1391, D18S535, D2S1338, D19S433, D6S477, D1S518, D14S306, D22S684, F13B, CD4, D12S391, D10S220 and D7S523 (the sequence of each loci is incorporated herein by reference). With the exception of D3 S1358, sequences for the STR loci of this invention are accessible to the general public through GenBank (see U.S. Pat. No. 6,090,558, incorporated herein by reference). Other STR loci have been developed by commercial manufacturers and studied extensively by forensic scientists. These include all of the GenePrint™ tretranucleotide STR systems from Promega Corporation (Madison Wis.).

Many different primers have been designed for various STR loci and reported in the literature. These primers anneal to DNA segments outside the DNA tandem repeat region to produce PCR products containing the tandem repeat region. These primers were designed with polyacrylamide gel electrophoretic separation in mind as a method of detection/measurement, because DNA separations have traditionally been performed by slab gel or capillary electrophoresis. STR multiplex analysis is usually performed with PCR amplification and detection of multiple markers. STR multiplexing is most commonly performed using spectrally distinguishable fluorescent tags and/or non-overlapping PCR product sizes. Multiplex STR amplification in one or two PCR reactions with fluorescently labeled primers and measurement with gel or capillary electrophoresis separation and laser induced fluorescence detection is a standard method. The STR alleles from these multiplexed PCR products typically range in size from 100-800 bp with commercially available lots.

Gel-based systems are capable of multiplexing the analysis of 2 or more STR loci using two approaches. The first approach is to size partition the different PCR product loci. Size partitioning involves designing the PCR primers used to amplify different loci so that the allele PCR product size range for each locus covers a different and separable part of the gel size spectrum. As an example, the PCR primers for Locus A might be designed so that the allele size range is from 250 to 300 nucleotides, while the primers for Locus B are designed to produce an allele size range from 340 to 410 nucleotides.

The second approach to multiplexing 2 or more STR loci on gel-based systems is the use of spectroscopic partitioning. Current state of the art for gel-based systems involves the use of fluorescent dyes as specific spectroscopic markers for different PCR amplified loci. Different chromophores that emit light at different color wavelengths provide a method for differential detection of two different PCR products even if they are exactly the same size, thus 2 or more loci can produce PCR products with allele size ranges that overlap. For example, Locus A with a green fluorescent tag produces an allele size range from 250 to 300 nucleotides, while Locus B with a red fluorescent tag produces an allele size range of 270 to 330 nucleotides. A scanning, laser-excited fluorescence detection device monitors the wavelength of emissions and assigns different PCR product sizes, and their corresponding allele values, to their specific loci based on their fluorescent color.

It is contemplated that a mass spectrometry approach to STR typing and analysis, examining smaller nucleic acid oligomers may be used because the sensitivity of detection and mass resolution are superior with smaller oligomers. Application of STR analysis to time of flight-mass spectrometry (TOF-MS) requires the development of primer sets that produce small PCR products 50 to 160 nucleotides in length, typically about 50 to 100 nucleotides in length. Amplified nucleic acids may also be used to generate single stranded products that are in the desired size range for TOF-MS analysis by extending a primer in the presence of a chain termination reagent. A typical class of chain termination reagent commonly used by those of skill in the art is the dideoxynucleotide triphosphates. Again, application of STR analysis to TOF-MS requires that the primer be extended to generate products of 50 to 160 nucleotides in size, and typically about 50 to 100 nucleotides in length (see U.S. Pat. No. 6,090,558 incorporated by reference).

A biotinylated cleavable oligonucleotide is used as a primer in each assay and is incorporated through standard nucleic acid amplification (i.e., PCR) methodologies into the final product which is measured in the mass spectrometer. This process is described in, for example, U.S. Pat. No. 5,700,642 and U.S. Pat. No. 6,090,558 (see also Butler et al., *International Journal of Legal Medicine* 112(1) 45-59 (1998)). The STR assay involves a PCR amplification step where one of the primers is replaced by a cleavable biotinylated primer. The biotinylated PCR product is then captured on streptavidin-coated magnetic beads for post-PCR sample cleanup and salt removal, followed by mass spectrometry analysis.

Single nucleotide polymorphisms (SNPs) represent another form of DNA variation that is useful for human identity testing. SNPs are the most frequent form of DNA sequence variation in the genomes of organisms and are becoming increasingly popular genetic markers for genome mapping studies and medical diagnostics. SNPs are typically bi-allelic with two possible nucleotides (nt) or alleles at a particular site in the genome. Because SNPs are less polymorphic (i.e., have fewer alleles) than the currently used STR markers, more SNP markers are required to obtain the same level of discrimination between samples. Approximately 30-50 unlinked SNPs may be required to obtain the matching probabilities of 1 in 100 billion as seen with the 13 CODIS STRs.

A SNP assay typically involves a three-step process: (1) PCR amplification (2) phosphatase removal of nucleotides, and (3) primer extension using a biotinylated cleavable primer with dideoxynucleotides for single-base addition of the nucleotide (s) complementary to the one(s) at the SNP site (Li et al., *Electrophoresis* 20(6): 1258-1265 (1999)).

Simultaneous analysis of multiple SNP markers (i.e. multiplexing) is possible by simply putting the cleavage sites at different positions in the various primers so that they do not overlap on a mass scale.

The two most common means for amplification is polymerase chain reaction (PCR), as described in U.S. Pat. Nos. 4,683,195, 4,683,202, 4,965,188 each of which is hereby incorporated by reference in its entirety. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at about 4° C. until use. Cells in other physiological fluids may also be assayed. When using any of these fluids, the cells in the fluid should be separated from the fluid component by centrifugation.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, buccal cells, or the like are isolated. The pellets are stored frozen at −200C until used (U.S. Patent Publication No. 20040253594 which is incorporated by reference).

The pellets may be resuspended in lysis solution from the PUREGENE® DNA isolation kit (Cat#D-5000, GENTRA, Minneapolis, Minn.) containing 100/ug/ml of proteinase K. After incubating at 55° C. overnight, DNA extraction is performed according to manufacturers recommendations. The DNA samples are resuspended in aqueous solution and stored at −200C.

When the sample contains a large number of cells, extraction may be accomplished by methods as described in Higuchi, "Simple and Rapid Preparation of Samples for PCR", in *PCR Technology*, p. 31-43 Ehrlich, H. A. (ed.), Stockton Press, New York.

A relatively easy procedure for extracting DNA for PCR is a salting out procedure adapted from the method described by Miller et al., *Nucleic Acids Res.* 16:1215 (1988), which is incorporated herein by reference. Nucleated cells are resuspended in 3 ml of lysis buffer (10 mM Tris-HCl, 400 mM NaCl, 2 mM Na2 EDTA, pH 8.2). Fifty μl of a 20 mg/ml solution of proteinase K and 200 ul of a 20% SDS solution are added to the cells and then incubated at 37° C. overnight. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is placed in distilled water and dissolved. (U.S. Patent Publication No. 20040253594 which is incorporated by reference).

Kits for the extraction of high-molecular weight DNA for PCR include PUREGENE® DNA Isolation kit (D-5000) GENTRA, a Genomic Isolation Kit A. S.A. P.® (Boehringer Mannheim, Indianapolis, Ind.), Genomic DNA Isolation System (GIBCO BRL, Gaithdrsburg, Md.), ELU-QUIK® DNA Purification Kit (Schleicher & Schnell, Keene, N.H.), DNA Extraction Kit (Stratagene, LaJolla, Calif.), TURBOGEN® Isolation Kit (Invitrogen, San Diego, Calif.), and the like. Use of these kits according to the manufacturer's instructions is generally acceptable for purification of DNA prior to practicing the methods of the invention (U.S. Patent Publication No. 20040253594 which is incorporated by reference).

The concentration and purity of the extracted DNA can be determined by spectrophotometric analysis of the absorbance of a diluted aliquot at 260 nm and 280 nm.

After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid (U.S. Patent Publication No. 20040253594 which is incorporated by reference).

In one embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to about 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the" art (see Kuhn et al., 1979, *CSH-Quantitative Biology,* 43:63-67; and Radding, 1982, *Ann. Rev, Genetics* 16:405-437, incorporated by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art (U.S. Patent Publication No. 20040253594 which is incorporated by reference).

Allele-specific PCR differentiates between target regions differing in the presence or absence of a variation or polymorphism. PCR amplification primers are chosen which bind only to certain alleles of the target sequence. This method is described by Gibbs, *Nucleic Acid Res.* 17:2437-2448 (1989) (U.S. Patent Publication No. 20040253594 which is incorporated by reference).

Further diagnostic screening methods employ the allele-specific oligonucleotide (ASO) screening methods, as described by Saiki et al., *Nature* 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wild-type allele (U.S. Patent Publication No. 20040253594 which is incorporated by reference).

Target regions of a subject's DNA can be compared with the mammary fluid sample by ligase-mediated allele detection. Ligase may also be used to detect point mutations in the ligation amplification reaction described in Wu and Wallace.,

*Genomics* 4:560-569 (1989). The ligation amplification reaction (LAR) utilizes amplification of specific DNA sequence using sequential rounds of template dependent ligation as described in Barany, Proc. Nat. Acad. Sci. 88:189-193 (1990) and U.S. Patent Publication No. 20040253594 which are incorporated by reference.

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Myers et al., Chapter 7 of Erlich, ed., *PCR Technology*, W.H. Freeman and Co., New York (1989) incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527 (1986), and Myers et al., in *Genomic Analysis, A Practical Approach*, K. Davies Ed. IRL Press Limited, Oxford, pp. 95-139 (1988). The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described by Myers in Chapter 7 of Erlich, *PCT Technology* Stockton Press, It is contemplated that at least 80% of the nucleotides in the GC clamp are either guanine or cytosine. The GC clamp may be at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. Nucleic acid fragments differing by a single base change will migrate through the gel to different positions, which may be visualized by ethidium bromide staining.

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis (see, e.g., U.S. Patent Application No. 20040253594).

The human leukocyte antigen complex (also known as the major histocompatibility complex) spans approximately 3.5 million base pairs on the short arm of chromosome 6. It is divisible into 3 separate regions which contain the class I, the class II and the class III genes. In humans, the class I HLA complex is about 2000 kb long and contains about 20 genes. Within the class I region exist genes encoding the well characterized class I MHC molecules designated HLA-A, HLA-B and HLA-C. In addition, there are nonclassical class I genes that include HLA-E, HLA-F, HLA-G, HLA-H, HLA-J and JLA-X as well as a new family known as MIC. The class II region contains three genes known as the HLA-DP, HLA-DQ and HLA-DR loci. These genes encode the chains of the classical class II MHC molecules designated HLA-DR, DP and DQ. In humans, nonclassical genes designated DM, DN and DO have also been identified within class II. The class III region contains a heterogeneous collection of more than 36 genes. Several complete components are encoded by three genes including the TNFs (see, e.g., U.S. Pat. No. 6,670,124 incorporated by reference).

Any given copy of human chromosome 6 can contain many different alternative versions of each of the preceding genes and thus can yield proteins with distinctly different sequences. The loci constituting the MHC are highly polymorphic, that is, many forms of the gene or alleles exist at each locus. Several hundred different allelic variants of class I and class II MHC molecules have been identified in humans. However, any one individual only expresses up to 6 different class I molecules and up to 12 different class II molecules.

The foregoing regions play a major role in determining whether transplanted tissue will be accepted as self (histocompatible) or rejected as foreign (histoincompatible). For instance, within the class H region, three loci, i.e., HLA-DR, DQ and DP are known to express functional products. Pairs of A and B genes within these three loci encode heterodimeric protein products which are multi-allelic and allorcactive. In addition, combinations of epitopes on DR and/or DQ molecules are recognized by alloreactive T cells. This reactivity has been used to define "Dw" types by cellular assays based upon the mixed lymphocyte reaction (MLR). It is contemplated that matching of the HLA type of the reference biological sample with the mammary fluid sample may be used to determine whether the mammary fluid sample originated from the donor.

One nucleic acid typing method for the identification of these alleles has been restriction fragment length polymorphism (RFLP) analysis discussed herein (see, also, U.S. Pat. No. 6,670,124).

In addition to restriction fragment length polymorphism (RFLP), another approach is the hybridization of PCR amplified products with sequence-specific oligonucleotide probes (PCR-SSO) to distinguish between HLA alleles (see, Tiercy et al., (1990) *Blood Review* 4:9-15). This method requires a PCR product of the HLA locus of interest be produced and then dotted onto nitrocellulose membranes or strips. Then each membrane is hybridized with a sequence specific probe, washed, and then analyzed by exposure to x-ray film or by colorimetric assay depending on the method of detection. Similarly to the PCR-SSP methodology, probes are made to the allelic polymorphic area responsible for the different HLA alleles. Each sample must be hybridized and probed at least 100-200 different times for a complete Class I and II typing. Hybridization and detection methods for PCR-SSO typing include the use of nonradioactive labeled probes, microplate formats, and the like (see, e.g., Saiki et al. (1989)

*Proc. Natl. Acad. Sci., U.S.A.* 86: 6230-6234; Erlich et al. (1991) *Eur. J. Immunogenet.* 18(1-2): 33-55; Kawasaki et al. (1993) *Methods Enzymol.* 218:369-381), and automated large scale HLA class II typing (see, e.g., U.S. Pat. No. 6,670,124).

Another typing method comprises sequence specific primer amplification (PCR-SSP) which may be used in the methods of the invention (see, Olemp and Zetterquist (1992) *Tissue Antigens* 39: 225-235). In PCR-SSP, allelic sequence specific primers amplify only the complementary template allele, allowing genetic variability to be detected with a high degree of resolution. This method allow determination of HLA type simply by whether or not amplification products (collectively called an "amplicon") are present or absent following PCR. In PCR-SSP, detection of the amplification products is usually done by agarose gel electrophoresis followed by ethidium bromide (EtBr) staining of the gel (see, e.g., U.S. Pat. No. 6,670,124).

Another HLA typing method is SSCP—Single-Stranded Conformational Polymorphism. Briefly, single stranded PCR products of the different HLA loci are run on non-denaturing Polyacrylamide Gel Electrophoresis (PAGE). The single strands will migrate to a unique location based on their base pair composition. By comparison with known standards, a typing can be deduced. It is the only method that can determine true homozygosity, (see, e.g., U.S. Pat. No. 6,670,124) (Orita et al., *Proc. Nat. Acad. Sci* 86:2766-2770 (1989)).

The identification of a DNA sequence can be made without an amplification step, based on polymorphisms including restriction fragment length polymorphisms ("RFLP") in a subject. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are typically labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetra-methyl-benzidine (TMB), fluorescein, and its derivatives, dansyl, umbelliferone and the like or with horse radish peroxidase, alkaline phosphatase and the like (see, e.g., U.S. Patent Publication No. 20040253594, U.S. Patent Publication No. 20050123947, which are incorporated by reference).

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation, combined with the teachings provided and incorporated herein.

The reagents suitable for applying the methods of the invention may be packaged into convenient kits. The kits provide the necessary materials, packaged into suitable containers. Typically, the reagent is a PCR set (a set of primers, DNA polymerase and 4 nucleoside triphosphates) that hybridize with the gene or loci thereof. Typically, the PCR set is included in the kit. Typically, the kit further comprises additional means, such as reagents, for detecting or measuring the detectable entity or providing a control. Other reagents used for hybridization, prehybridization, DNA extraction, visualization etc. may also be included, if desired.

Other Identity Markers Profiles

It is further contemplated that the mammary fluid sample may be tested for self-antigens (or other peptides and polypeptides) present in the mammary fluid to establish a self-antigen profile (identity marker profile). The self-antigen profile of the mammary fluid sample will be compared to the reference self-antigen profile for the individual human. A match or identity of the self-antigen profile will indicate that the mammary fluid was obtained from the specific subject.

The various antigens that determine self are encoded by more than 40 different loci, such as the major histocompatibility complex (MHC), also called the human leukocyte antigen (HLA) locus, and the blood group antigens, such as ABO.

Methods are known in the art for screening humans for ABO blood group type. The blood-group antigens are expressed on red blood cells, epithelial cells and endothelial cells.

Testing for HLA type can be conducted by methods known in the art such as serological and cellular typing.

It is contemplated that the antigens could be identified by a microcytotoxicity test. In this test, white blood cells are distributed in a microtiter plate and monoclonal antibodies specific for class I and class II MHC antigens are added to different wells. Thereafter, complement is added to the wells and cytotoxicity is assessed by uptake or exclusion to various dyes (e.g., trypan blue or eosinY) by the cells. If the white blood cells express the MHC antigen for a particular monoclonal antibody, then the cells will be lysed on addition of complement and these dead cells will take up the dye (see, Terasaki and McClelland, (1964) *Nature,* 204:998 and U.S. Pat. No. 6,670,124). HLA typing based on antibody-mediated microcytotoxicity can thus indicate the presence or absence of various MHC alleles (See Kuby *Immunology* 4th Ed., Freeman and Company, pp 520-522).

The detection of antigens may be selected from, but is not limited to, enzyme-linked immunosorbent assay, solid phase radiobinding immunoassays where the antibodies may be directed against soluble antigens or cell surface antigens, autoradiography, competitive binding radioimmunoassay, immunoradiometric assay (IRMA) electron microscopy, peroxidase antiperoxidase (PAP) labeling, fluorescent microscopy, alkaline phosphatase labeling and peroxidase labeling.

In the case where the detection method (s) use optical microscopy, the cells from the biological sample or the mammary fluid sample are mounted and fixed on a microscope slide. In this case, the step of detecting the labelled antibody is detecting a resulting colouration of the self-antigen with an optical microscope (see, e.g., U.S. Pat. No. 6,376,201).

The following example provides an embodiment of the methods described herein and should not be understood as restrictive.

Example 1

Testing of a Human Breast Milk Donor

A woman who wishes to donate her breast milk will provide a biological reference sample prior to (or at the time of) her first donation. The biological sample will include a convenient tissue type, e.g., blood, cheek cell, hair etc. The sample will be donated under supervision of another individual(s), e.g., bank milk personnel. The sample will be labeled for later reference. The reference sample will be tested for a specific marker profile, e.g., nucleic acid and/or peptide profile. The sample will be tested for one or more markers. Results of the tests will be stored, e.g., on a computer-readable medium for future reference. Any remaining sample will be stored. The woman can also be screened (using the reference sample or another sample) for, e.g., drug use, viruses, bacteria, parasites, and fungi etc., to determine her health. The woman will be given a label corresponding to the reference sample to keep with her and use with her donated milk.

Alternatively, the sample will be stored without testing, and will be tested at a later date, for example, together with the donated breast milk.

The woman will express her milk for donation and either forward the milk to the milk bank or processing facility or store the milk in her refrigerator, e.g., the freezer, for donation with other samples at a later date. The donated milk will be labeled with the label given to the woman and matching the reference sample.

A sample of the donated milk that arrives at the milk bank or processing facility will be tested for at least one of the same markers as the reference sample. The marker profile of the reference sample will be compared to the marker profile of the donated milk sample. If the profiles will match, the identity of the donor will be confirmed. If the profiles will not match, the results will be an indication that the donated milk is contaminated with another woman's milk or that it does not come from the woman whose reference sample was taken.

The milk whose provenance (i.e., origin) will be confirmed by the matched profiles will be further processed, e.g., pasteurized, e.g., into human milk fortifiers, standardized human milk compositions, and/or human lipid compositions. Such compositions will be administered to human infants, e.g., premature infants, whose mothers may not be able to provide them with adequate nutrition.

The reference sample and/or results of the reference sample tests will be stored for any future donation by the corresponding mother.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining whether a donated mammary fluid was obtained from a specific subject, the method comprising:
   (a) testing a donated biological sample from the specific subject to obtain at least one reference identity marker profile for at least one marker;
   (b) testing a sample of the donated mammary fluid to obtain at least one identity marker profile for the at least one marker in step (a);
   (c) comparing the identity marker profiles,
   wherein a match between the identity marker profiles indicates that the mammary fluid was obtained from the specific subject; and
   (d) processing the donated mammary fluid whose identity marker profile has been matched with a reference identity marker profile, wherein the processed donated mammary fluid comprises a human protein constituent of 11-20 mg/mL; a human fat constituent of 35-55 mg/mL; and a human carbohydrate constituent of 70-120 mg/mL.

2. The method of claim 1, wherein the mammary fluid is human breast milk.

3. The method of claim 1 wherein the processing comprises:
   (a) filtering the milk;
   (b) heat-treating the milk;
   (c) separating the milk into cream and skim;
   (d) adding a portion of the cream to the skim; and
   (e) pasteurizing.

4. The method of claim 1, wherein the composition further comprises one or more constituents selected from the group consisting of: calcium, chloride, copper, iron, magnesium, manganese, phosphorus, potassium, sodium, and zinc.

5. The method of claim 1, wherein processing comprises separating the milk into a cream portion and a skim portion, processing the cream portion, and pasteurizing the cream portion.

6. The method of claim 1, further comprising nucleic acid typing, wherein the nucleic acid typing comprises a method selected from the group consisting of: STR analysis, HLA analysis, multiple gene analysis, and a combination thereof.

7. The method of claim 1, wherein the donated mammary fluid is frozen.

8. The method of claim 1, wherein the mammary fluid sample comprises a mixture of one or more mammary fluid samples.

9. The method of claim 1, wherein the donated biological sample is selected from a group consisting of: milk, saliva, buccal cell, hair root, and blood.

10. The method of claim 1, wherein steps (a) through (c) are carried out at a human breast milk donation center or at a milk processing facility.

11. The method of claim 1, wherein steps (a) and (b) are carried out at different facilities.

12. The method of claim 11, wherein step (a) is carried out at a human breast milk donation facility and step (b) is carried out at a milk processing facility.

13. A method for processing a donated human breast milk obtained from a specific subject comprising:
   (a) testing a donated biological sample from the specific subject to obtain at least one reference identity marker profile for at least one marker;
   (b) testing a sample of the donated human breast milk to obtain at least one identity marker profile for the at least one marker in step (a);
   (c) comparing the identity marker profiles of steps (a) and (b), wherein a match between the identity marker profiles indicates that the donated human breast milk was obtained from the specific subject;
   (d) processing the donated human breast milk whose identity marker profile has been matched with a reference identity marker profile, wherein the processing comprises:
      (i) filtering the donated human breast milk; (ii) heat treating the donated human breast milk;
      (iii) separating the donated human breast milk into cream and skim; (iv) adding a portion of the cream to the skim to form a human milk composition; and (v) pasteurizing the human milk composition to produce a processed human breast milk composition;
   and wherein the processed donated human breast milk comprises a human protein constituent of 11-20 mg/mL; a human fat constituent of 35-55 mg/mL; and a human carbohydrate constituent of 70-120 mg/mL.

14. A processed human milk composition suitable for administration to an infant made by the process of claim 13.

15. The method of claim 13, wherein the method further comprises adding to the processed human breast milk one or more constituents selected from the group consisting of: calcium, chloride, copper, iron, magnesium, manganese, phosphorus, potassium, sodium, and zinc.

16. The method of claim 13, wherein the testing of the donated human breast milk of step (b) and the testing of the donated biological sample of step (a) comprises nucleic acid typing selected from the group consisting of: STR analysis, HLA analysis, multiple gene analysis, and a combination thereof.

17. The method of claim 13, wherein the donated biological sample is selected from a group consisting of: milk, saliva, buccal cell, hair root, and blood.

18. The method of claim 13, wherein steps (a) through (c) are carried out at a human breast milk donation center or at a milk processing facility.

19. The method of claim 13, wherein steps (a) and (b) are carried out at different facilities.

20. The method of claim 19, wherein step (a) is carried out at a human breast milk donation facility and step (b) is carried out at a milk processing facility.

* * * * *